United States Patent [19]

Vlock

[11] Patent Number: 4,738,669

[45] Date of Patent: Apr. 19, 1988

[54] FLUID DISPENSER USING CAPILLARY ACTION

[76] Inventor: David G. Vlock, 12 Fifth Ave., New York, N.Y. 10011

[21] Appl. No.: 9,841

[22] Filed: Jan. 30, 1987

Related U.S. Application Data

[63] Continuation of Ser. No. 812,595, Dec. 23, 1985, abandoned, which is a continuation-in-part of Ser. No. 643,912, Aug. 24, 1984, Pat. No. 4,583,982.

[51] Int. Cl.$^4$ .............................................. A61M 35/00
[52] U.S. Cl. ..................................... 604/289; 604/310; 433/80; 222/420; 401/256
[58] Field of Search .............. 604/289, 294, 295, 290, 604/310; 222/420, 421, 575, 469; 433/80; 15/437, 438, 445, 447; 401/256, 257, 267, 261, 265

[56] References Cited

U.S. PATENT DOCUMENTS

| | | | |
|---|---|---|---|
| 371,133 | 10/1887 | Fisher | 401/256 |
| 2,842,100 | 7/1958 | Hodges | 401/256 |
| 4,217,060 | 8/1980 | Ikegami et al. | 401/265 |
| 4,583,982 | 4/1986 | Vlock | 604/310 |

FOREIGN PATENT DOCUMENTS 167755  2/1906  Fed. Rep. of Germany ........ 15/447

Primary Examiner—C. Fred Rosenbaum
Assistant Examiner—J. L. Kruter
Attorney, Agent, or Firm—Lawrence Rosen

[57] ABSTRACT

A fluid dispenser having a handle portion supporting at least three spaced-apart, flexible prongs or tines that meet at a pyramidal apex to form a fluid-containing cradle. The cradle holds a precise amount of fluid therein by surface tension between the prongs and the fluid. The small cradle pocket formed at the apex of these prongs has a capillary channel disposed ahead of it, which terminates at the tip of the prongs. When the tip of the prongs are contacted to a body surface in question and slightly flexed, fluid will flow from the cradle through the capillary channel to this surface.

7 Claims, 2 Drawing Sheets

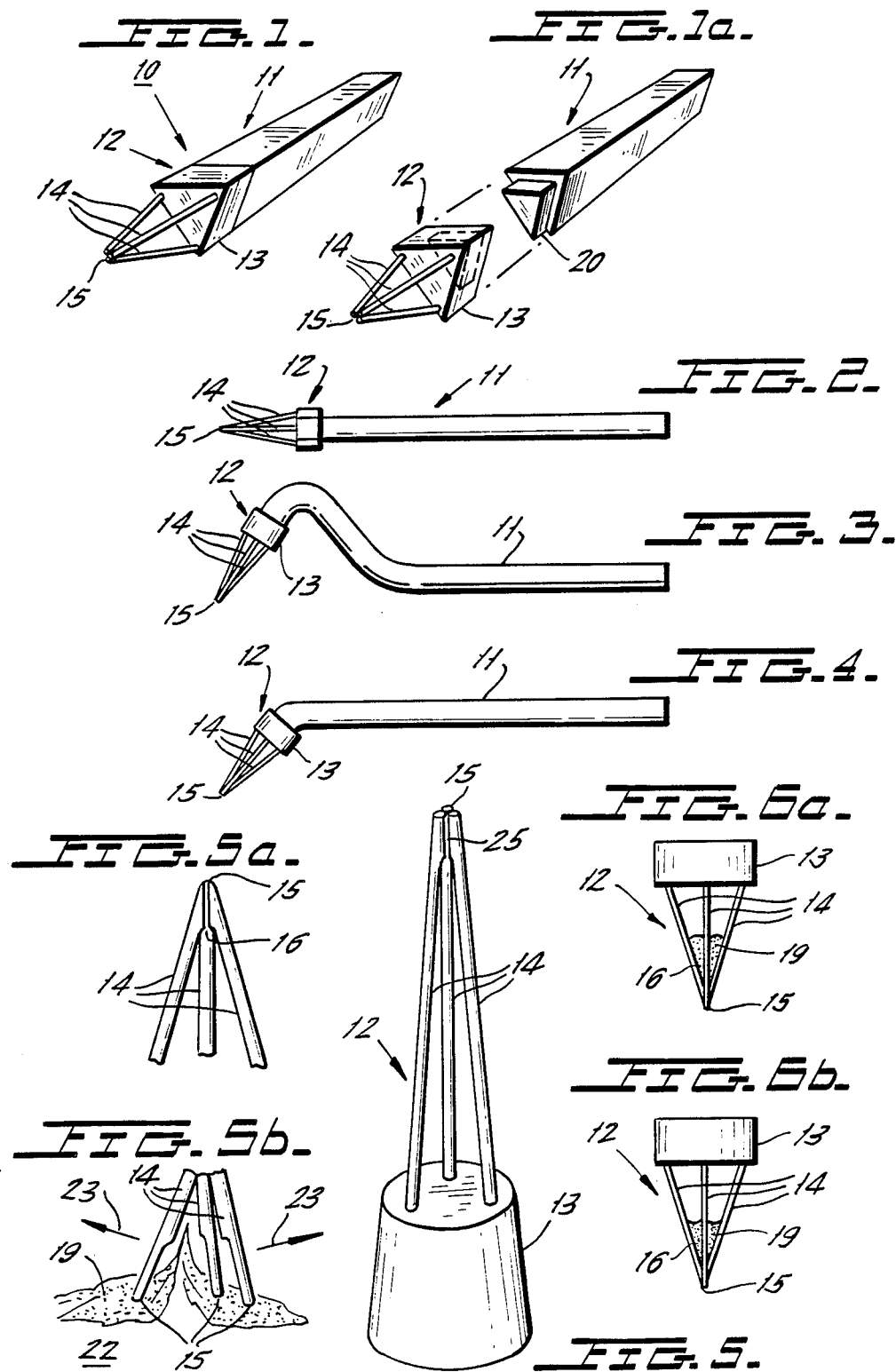

FLUID DISPENSER USING CAPILLARY ACTION

RELATED APPLICATION

This application is a continuation of Ser. No. 812,595, filed Dec. 23, 1985 now abandoned, which is a continuation-in-part of Ser. No. 643,912, filed Aug. 24, 1984, now U.S. Pat. No. 4,583,982.

FIELD OF THE INVENTION

The invention relates to a fluid dispensing device for placing a quantity of fluid upon a body surface, and more particularly to a hand-held tool for dispensing a fluid to a body surface in a precise manner.

BACKGROUND OF THE INVENTION

In dental, medical and surgical applications, it is often required to place a medicine or medicament upon a body surface such as the gums, skin, epithelium, cheek or tongue. Often only a small amount of fluid is needed, particularly when applying caustics and astringents. These types of fluids require precise placement to the effected areas without spillage. Often exacting amounts are required in order to prevent dripping and run over into non-affected regions.

Hand-held dispensing tools have been invented that will extract fluid from a fluid source such as a vial or bottle, and which are capable of placing the fluid upon a body surface. Such devices are illustrated in U.S. Pat. Nos. 1,632,686; issued Jun. 14, 1927 and 1,586,302, issued May 25 1926.

In both the above patents, a hand-held tool is described featuring a resilient tubular tip for carrying and dispensing fluids. While these hand-held devices accomplish placing small amounts of fluid upon various body surfaces, they cannot precisely extract a given quantity of fluid from a bottle or vial. The delivered fluid is always a little more or a liitle less than what may be required. Delivery of the fluid is not carefully controlled.

The present invention features a fluid dispensing tool that is designed to extract a precise amount of fluid from a container and then accurately deliver that fluid exactly to the affected region.

In addition, the invention is useful with a wide range of fluids having different viscosities. As such, the invention enjoys a universality and versatility not commonly found in similar devices.

SUMMARY OF THE INVENTION

The invention features a fluid dispenser having a handle portion supporting at least three spaced-apart, flexible prongs or tines that meet at a pyramidal apex to form a fluid-containing cradle. The cradle holds a precise amount of fluid therein by means of the surface tension between the prongs and the fluid. The small cradle pocket formed at the apex of these prongs has a capillary channel disposed ahead of it, which terminates at the tip of the prongs. When the tip of the prongs are contacted to a body surface in question and slightly flexed, fluid will flow from the cradle through the capillary channel to this surface. Thus, a precise amount of fluid is accurately and precisely placed to the desired region.

The amount or quantity of the fluid held in the cradle pocket will depend upon the apex angle, the number of prongs and the choice of materials that influence the surface tension forces.

The prongs can be mounted on a truncated base which in turn attaches to the handle by means of a key or male/female connection. The base and the prongs are detachable from the handle, so that sanitary and asceptic conditions can be maintained between patients, i.e. the fluid carrying and discharging member carrying the new prongs is attached for each new use.

The cradle formed by the prongs will extract a precise quantity of fluid from a vial or bottle of fluid when immersed therein and subsequently removed.

In accordance with a particularly preferred feature the dispenser has at least one prong or tine located approximately in the center of the base carrying the multiplicity of spaced apart, flexible prongs or tines. Generally, in this embodiment at least four prongs or tines will be utilized.

It is an object of the invention to provide an improved fluid dispenser.

It is another object of this invention to provide a fluid dispensing device to place accurately a precise quantity of fluid to a body surface.

These and other objects of the invention will be better understood and will become more apparent with reference to the following detailed description considered in conjunction with the accompanying drawings.

BRIEF DESCRIPTION OF THE DRAWINGS

FIG. 1 is a perspective view of the fluid dispensing device of this invention.

FIG. 1a is a perspective exploded view of the inventive device shown in FIG. 1.

FIGS. 2 through 4 illustrate respective embodiments of the device illustrated in FIG. 1.

FIG. 5 depicts an enlarged perspective view of the forward section of the device shown in FIG. 1.

FIG. 5a illustrates an enlarged view of the apex of the forward section shown in FIG. 5.

FIG. 5b shows an enlarged, exaggerated view of the apex of the forward section depicted in FIG. 5a in a fluid discharging mode.

FIGS. 6a and 6b depict schematic views of the apex of the forward section shown in FIG. 5 in a fluid supporting mode. FIG 6a shows the fluid with a concave menescus and FIG. 6b depicts the fluid with a convex meniscus.

FIG. 8b is a perspective view of an illustrative dispensing device utilizing the fluid carrying member shown in FIG. 8a.

FIG. 9b is a perspective view of an illustrative dispensing device utilizing the fluid carrying member shown in FIG 9a.

DETAILED DESCRIPTION OF THE INVENTION

Figures 7, 8A, 9A:
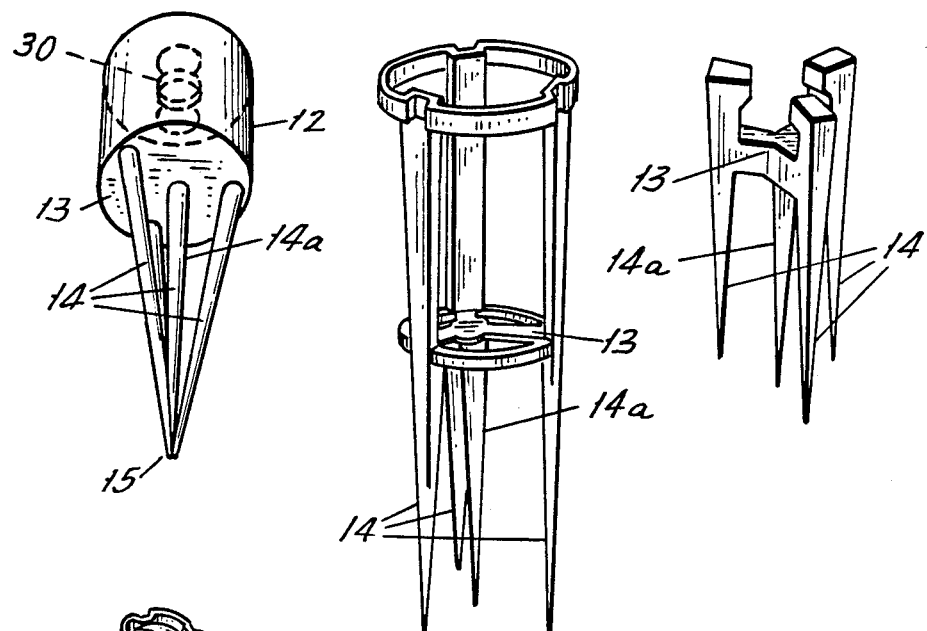
FIG. 7 is a perspective view of another fluid dispensing device according to the invention.
FIG. 8a is an enlarged view of the fluid carrying and discharging member for use with the dispensing device.
FIG. 9a is an enlarged view of another fluid carrying and discharging member for use with the dispensing device.

Generally speaking, the invention pertains to a fluid dispensing device wherein precise amounts of fluid are extracted from a fluid source and then accurately placed upon a body surface.

Now referring to FIG. 1, the fluid dispensing device 10 of this invention is shown. The device 10 is comprised of a handle portion 11 and a fluid carrying and discharging section 12. The fluid carrying and discharging section 12 includes a base 13 in which a number of spaced apart, flexible prongs or tines 14 are affixed. The prongs 14 are arranged in the form of a pyramidal skeleton. Although three prongs 14 are illustrated, the device can function with more than three prongs, i.e. with a multiplicity of prongs. In accordance with an especially preferred embodiment one of the prongs is centrally located on the base carrying member. This central prong ensures that a variety of fluids can be picked up easily and enhances the ability of the device to hold the fluid for substantial periods prior to discharge.

However, at least three prongs are required to fulfill the unique fluid carrying capacity of the invention.

The prongs 14 form an apex 15 at their tip, wherein each prong 14 is closely adjacent but not attached to its neighboring prongs as may be seen in more detail in FIGS. 5 and 5a.

FIG. 5 depicts an enlarged view of the fluid carrying and discharging section 12 of FIG. 1.

FIG 5a illustrates a further enlarged view of the apex 15 of the prongs 14.

The prongs 14 form a fluid carrying cradle 16 at the apex 15. The tips of the prongs 14 are in close proximity to or slightly touch each other, but are never joined, to form a narrow capillary channel 18 with its neighbor prongs directly ahead of the cradle 16.

When the apex 15 of the prongs 14 is immersed and removed from a fluid, a small precise quantity of fluid 19 will be trapped in cradle 16, as is shown schematically in FIG. 6a. The fluid quantity 19 is trapped in cradle 16 by means of the surface tension between the fluid 19 and the prongs 14. In most cases, the fluid quantity 19 will form a concave meniscus between the prongs 14, as shown in FIG. 6a. However, with the use of hydrophobic materials for prongs 14, like teflon, the meniscus may actually be convex, as depicted in FIG. 6b.

Depending upon the number of prongs 14 used in the fluid section 12 and the types of materials and angles chosen for prongs 14, the quantity of fluid 19 can be varied to provide a precise amount of fluid extracted and carried in cradle 16.

The invention contemplates making fluid or member section 12 detachable from the handle 11, as shown in more detail in FIG. 1a. The section 12 is made detachable for the reasons that different sections 12 can be used for different quantities of fluids. Also, sanitary and aseptic conditions require a different section 12 for each patient, i.e. section 12 can be discarded after each use.

Section 12 can attach to handle 11 by means of a male-female connection, such as a triangular key 20 and mating triangular hole 21 as shown. After each use, section 12 can be removed from the handle 11, and a new fluid section 12 can be attached to handle 11.

The fluid quantity 19 can be precisely placed on a body surface, such as the skin or epithelium by touching the apex 15 of the prongs 14 to the body surface 22, as shown in the exaggerated enlarged view of FIG. 5b. The fluid quantity 19 will be drawn from the cradle 16 down the capillary channel 25 to flood the desired surface 22 by flexing the prongs 14 (arrows 23) to disrupt the surface tension forces holding the fluid 19 in cradle 16. The fluid will flow by capillary action in any desired direction, including antigravitationally and could possibly be used in outer space applications.

The shape of the handle 11 and the angle of section 12 can be varied, as shown in the alternate embodiments of FIGS. 2 through 4.

The shape of the handle 11 can be round as shown in FIGS. 2 and 3, or square or triangular, as illustrated in FIGS. 4 and 1, respectively. Different handle shapes may be more conveniently held in accordance with the preference of the user.

In addition, the mating angle between section 12 and handle 11 may be varied for placing fluid on surfaces that are not easily accessible. FIG. 3 illustrates a curved handle 11 and an angled section 12. FIG. 4 depicts an angled section 12 with a straight handle 11.

In keeping with the design or shape of the handle 11, the base 13 of section 12 can be a truncated cone, or a square or triangular prism.

The prongs or tines 14 can be made of plastics or other inert materials that are fexilble, sturdy, and chemically resistant. A multiplicity of prongs or tines can be utilized with one or more located approximately at the center of the base member.

The handle and base portions of the device 10 can also be made from plastics that are strong and sturdy. It should be further understood that a unitary dispenser is also contemplated where the handle, the fluid carrying and discharging member, including the multiple prongs or tines, are fabricated or molded from the same or compatible materials. This type of dispenser will generally be discarded after each use for the same purpose or for the same patient.

Figure 8B:
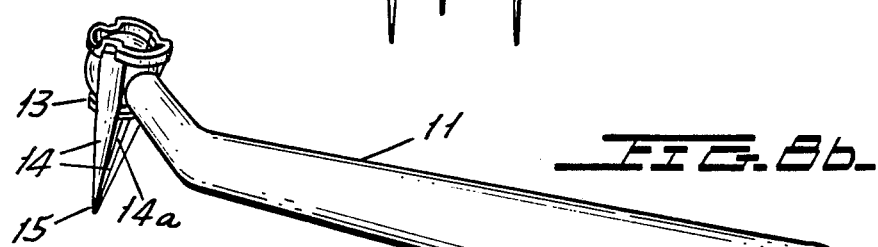
Figure 9B:
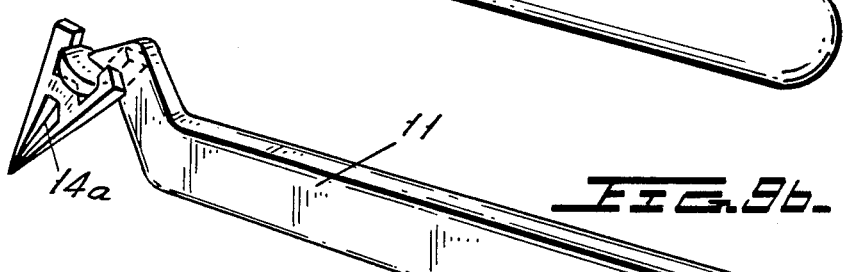
Figure 10:
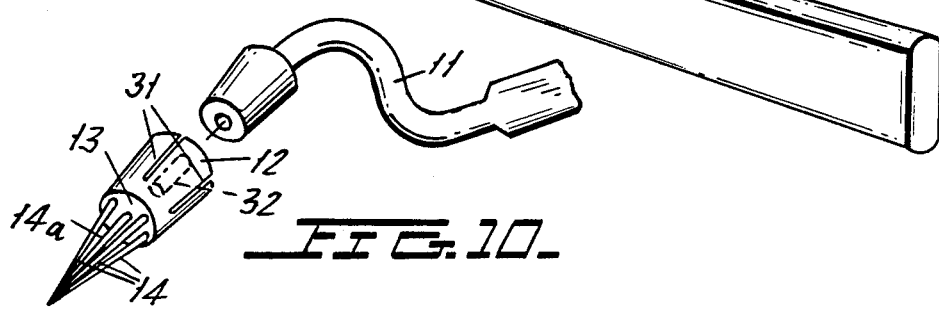
FIG. 10 is a perspective exploded view of another embodiment of a dispensing device according to the invention.

Devices of the invention which yield improved results are illustrated in FIGS. 7 through 10. A prong or tine 14 is positioned approximately in the middle or centrally on base 13 of fluid carrying and discharging section 12 that is attachable to handle 11 in a varieiy of ways. As shown in FIGS. 8b, 9b, and 10 the shape of the handle may vary widely. FIGS. 7 and 10 show holes 30 (not shown specific in FIG. 10) with resulting means that make members 12 easily attachable to handles 11. Thus, FIG. 7 specifically illustrates a hole 30 for handle 11 insert with a high and low frictional snap keeper.

The fluid carrying and discharging member 12 shown in FIGS. 8a and 9b are so constructed that when they are snapped on to the ends of handles 11 shown in FIGS. 8b and 9b respectively, the resulting pressure forms the desired apex 15, where the tips of the prongs are so proximate that they almost touch or touch lightly.

In FIG. 10 the sides of the liquid carrying member have slits 31 and a post 32 for insertion into handle 11 and to exert pressure on the prongs 14 that maintain apex 15.

In the improved device it has been found helpful, but not essential, to maintain a sharp acute angle, e.g. about an 8 degree angle, between the center prong 14a and each outside prong; the measurement being taken from the center long axis of each prong.

Where it is desired to sterilize the instrument, such plastics must be temperature resistant. Other materials such as titanium will provide inertness, strength and temperature and chemical resistance.

Having thus described the invention, what is desired to be protected by Letters Patent is presented by the appended claims.

What is claimed is:

1. A dental fluid dispenser for precisely placing medicine upon a gum surface comprising a handle portion means for supporting a circular base portion, said circular base portion supporting three peripherally spaced apart plastic flexible elongated prong member means that substantially form an open spaced, non-attached pyramidal apex at their respective distal ends, a fourth flexible plastic elongated prong member means extending longitudinally from a central portion of said circular base portion into said pyramidal apex in a spaced relationship, said prong member means touching but not joined to form a capillary cradle means at said apex for holding medicine by surface tension and upon which flexural contact with said gum surface will discharge the medicine.

2. The fluid dispenser of claim 1 wherein said prongs are mounted upon a base supported by said handle portion.

3. The fluid dispenser of claim 2 wherein said base is truncated.

4. The fluid dispenser of claim 2 wherein said base is keyed to said handle portion.

5. The fluid dispenser of claim 1, wherein said cradle will extract fluid from a fluid source upon immersion into said fluid source.

6. The fluid dispenser of claim 5 wherein said cradle holds and discharges a given quantity of fluid.

7. The fluid dispenser of claim 1 wherein said handle portion and base portion are unitary.

* * * * *